(12) United States Patent
Hansen et al.

(10) Patent No.: US 6,297,422 B1
(45) Date of Patent: Oct. 2, 2001

(54) DRESSING COMPRISING A MAIN PART AND A HANDLE PART

(75) Inventors: Grazyna Hansen, Farum; Lars Bo Madsen, Gentofte, both of (DK)

(73) Assignee: Colorplast A/S, Humlebaek (DK)

(*) Notice: Subject to any disclaimer, the term of this patent is extended or adjusted under 35 U.S.C. 154(b) by 0 days.

(21) Appl. No.: 09/147,299

(22) PCT Filed: May 22, 1997

(86) PCT No.: PCT/DK97/00233

§ 371 Date: Nov. 23, 1998

§ 102(e) Date: Nov. 23, 1998

(87) PCT Pub. No.: WO97/43991

PCT Pub. Date: Nov. 27, 1997

(30) Foreign Application Priority Data

May 22, 1996 (DK) .................................................. 0597/96

(51) Int. Cl.[7] ........................................................ A61F 13/00
(52) U.S. Cl. .................................. 602/57; 602/54; 602/58
(58) Field of Search .................... 602/41–59; 128/888, 128/889; 604/304

(56) References Cited

U.S. PATENT DOCUMENTS

| | | | |
|---|---|---|---|
| 4,413,621 | * 11/1983 | McCracken et al. | 128/156 |
| 4,753,232 | 6/1988 | Ward | 128/156 |
| 4,952,618 | 8/1990 | Olsen | 524/17 |
| 5,099,832 | * 3/1992 | Ward | 602/57 |

FOREIGN PATENT DOCUMENTS

| | | |
|---|---|---|
| 0 081 987 | 6/1983 | (EP) . |
| 0 507 459 | 10/1992 | (EP) . |
| 0 613 669 | 9/1994 | (EP) . |
| 0 638 301 | 2/1995 | (EP) . |
| WO94/26514 | 11/1994 | (WO) . |

OTHER PUBLICATIONS

Tegasorb™ Ulcer Dressing, 3M health Care, St. Paul, Minnesota Jan. 1989.

* cited by examiner

*Primary Examiner*—Kim M. Lewis
(74) *Attorney, Agent, or Firm*—Jacobson Holman, PLLC

(57) ABSTRACT

A dressing comprising a main part and a handle part. The main part comprising an adhesive layer, a release liner and a carrier layer optionally covered by a protective layer. The handle part comprises at least one table member, said tab member being designed for use as a "non touch" grip for applying the dressing to the skin without touching the adhesive surface of the main part. The tab member comprises one or more layers and has at least one layer in common with the main part of the dressing. Further, the length of an intermediate zone between the handle part and the main part is less than 20% of the length of the periphery of the main part. Still further, the handle part may be provided with at least one additional layer. Finally, there may be provided at least one notch in an intermediate zone between the handle part and the main part of the dressing in order to facilitate removal of the tab member during or after applying the dressing.

19 Claims, 6 Drawing Sheets

DRESSING COMPRISING A MAIN PART AND A HANDLE PART

FIELD OF THE INVENTION

The present invention relates to a dressing comprising at least one tab member, said tab being designed for use as a "non touch" grip for applying the dressing to the skin without touching the adhesive layer, wherein said tab is removed during or after application of the dressing. Further the invention relates to methods for manufacturing such dressings.

BACKGROUND OF THE INVENTION

As it is commonly known thin wound dressings are difficult to apply to wounds, especially in curved areas, without wrinkling or sticking to themselves or to the users fingers. It is desirable to apply all kinds of dressings without touching the adhesive layer in order to avoid reducing the adhesiveness. Because of the risk of introducing bacterial to the wound it is desirable to apply a dressing to a patient's skin without touching the surface of the dressing that is to come into contact with the skin. The prior art discloses several methods for facilitating handling of a wound dressing.

U.S. Pat. No. 4,753,232 discloses a "handle" portion along one edge of the dressing, where the handle is formed from a tearable material or the dressing may have a perforation line along the edge. After the dressing is applied, the handle may be removed by tearing, or it may carry an adhesive coating so that it may be adhered to the skin of the patient. In the case where the handle is torn off, it will leave burrs of adhesive material along the tearing line. These burrs of adhesive material will adhere to e.g. the fingers of the person who applies the dressing, garments or anything which comes into contact with the edges resulting in loosening of the dressing. If the handle carries an adhesive and is adhered to the skin of the patient it renders the dressing large and clumsy when applied.

U.S. Pat. No. 4,413,621 and European Patent Application No. 0 081 987 A1 disclose a wound dressing which comprises a flexible adhesive coated sheet having a pair of adhesive-free "handle" portions, formed of the same material as the flexible sheet, adjacent to perforation lines on opposed side edges of the sheet. These "handle" portions can be detached from the sheet, after application of the dressing, by separating along the perforation lines. The removal of the handles needs a force which can result in the lifting of the edges of the dressing. Further this dressing can not be used for forming an anatomical dressing.

WO patent publication No. 94/26514 discloses a self-adhesive laminate which can be used as a conventional square shaped wound dressing in which a thin transparent film has a layer of skin adhesive on one side, shielded before use by a cover sheet. The cover sheet and the backing sheet are linked by a hinge. To apply the dressing, the cover sheet is peeled off and left hanging by the hinge and the film is adhered to the patient while holding a tab opposite the hinge. After application the tab is removed from the film by tearing along perforations parallel to one of the four edges. This dressing is held stable and is protected against stretching during application, therefore it cannot be used for forming an anatomical dressing. Further the edge which has been torn off shows a relatively long line of exposed adhesive and will have the disadvantage to stick to everything, resulting in peeling off of the dressing.

EP patent application No. 0638301 discloses a medical dressing with semipeperipheral delivery system and methods therefor. The dressing system disclosed herein comprises a backing layer, an adhesive material overlying the backing layer and a release liner overlying the adhesive, wherein said medical system further comprises a final dressing portion and a semiperipheral support portion surrounding said dressing portion, said support portion being partially defined by at least one unsupported edge, said one or more edges extending from a first end to a second end of said semiperipheral support portion. The separation line where the support portion is removed after application of the dressing is inconveniently long and will tend to stick to everything.

Finally, EP patent application No. 0507459 discloses a combined adhesive, strip and transparent dressing delivery system. This system offers an application procedure where touching of the adhesive surface of the adhesive strip is very difficult to avoid. This gives a serious drawback because of the risk of contamination. A further problem associated with the state of the art dressings described above is that they are complicated to manufacture and some of them leave a disadvantageous edge with a non appellant appearance along the tearing or perforation line.

BRIEF DESCRIPTION OF THE INVENTION

The object of the invention is thus to provide a dressing with at least one tab member ensuring an easy handling of a dressing without touching the adhesive, and in which the problems associated with the removing of tabs from the known dressings is avoided.

The present invention relates to a dressing consisting of a main part and a handle part, said main part comprising an adhesive layer, a release liner and a carrier layer optionally covered by a protective layer, wherein the handle part comprises at least one tab member, said tab member being designed for use as a "non touch" grip for applying the dressing to the skin without touching the adhesive surface of the main part, wherein the tab member comprises one or more layers and has at least one layer in common with the main part of the dressing. Further, the dressing may optionally be provided with at least one notch in an intermediate zone between the handle part and the main part of the dressing.

In a further aspect the invention relates to methods for manufacturing such a dressing.

BRIEF DESCRIPTION OF THE DRAWINGS

The invention is explained in detail below with reference to the drawings, in which.

Figure 1:
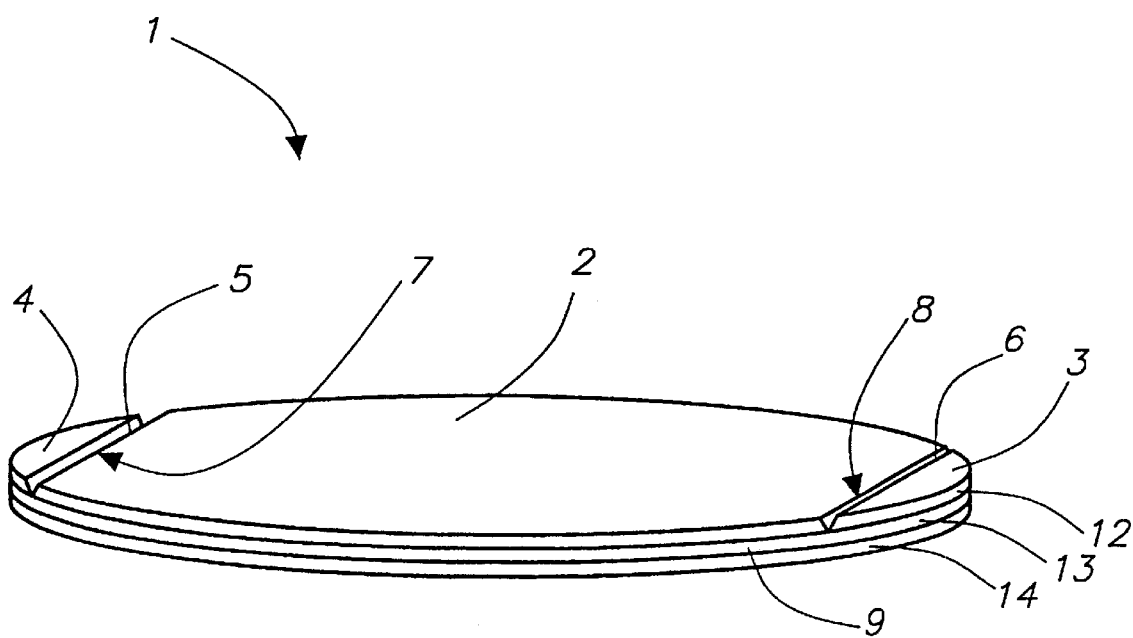
FIG. 1 is a schematic view of a wound dressing according to the invention with two tab members and wherein a notch is provided along each of the intermediate zones between the main part of the dressing and the tab members.

The drawings are all schematic examples of specific embodiments of the invention and are not to be considered as being limiting for the scope of the invention in any way. The ratio between the thicknesses of the different layers of the dressing are not meant to be limited to the examples given in the drawings. The thickness of each individual layer may vary according to a predetermined pattern e.g. one or more layers may have reduced thickness along the intermediate zone and/or bevelled edges.

DETAILED DESCRIPTION OF THE INVENTION

The dressing according to the invention is characterised in that it comprises a main part and a handle part, said main part comprising an adhesive layer, a release liner and a carrier layer optionally covered by a protective layer and said handle part comprises at least one tab member, said tab member being designed for use as a "non touch" grip for applying the dressing to the skin without touching the adhesive surface of the main part, wherein the tab member comprises one or more layers and having at least one layer in common with the main part of the dressing and wherein the length of an intermediate zone (the line of conjunction) between the handle part and the main part is less than 20% of the length of the periphery of the main part.

It is advantageous when the tab members and the main part of the dressing do not have all layers in common, as it reduces the force which need to be applied in order to remove the tab members after applying the dressing. When the necessary force is reduced the above problems regarding loosening of the dressing, adhesive edges etc. are reduced considerably. Further it has shown to be particularly advantageous when the length of the intermediate zone between the handle part and the main part is less than 20% of the length of the periphery of the main part. It necessitates a considerable smaller force when tearing of the handle part after application. Further the torn off edge is sufficiently short to essentially eliminate problems with sticking to other objects which may cause peeling off of the dressings. Furthermore, the risk of providing a non appellant appearance along the tearing or perforation line is minimised.

An embodiment of the invention is characterised in that the handle part is provided with at least one additional layer. Such layer is provided in order to prevent the tab member from sticking to any surface e.g. the applying hand or finger.

According to another embodiment of the invention the dressing is characterised in that there is provided at least one notch in an intermediate zone between the handle part and the main part of the dressing in order to further facilitate removal of the tab member during or after applying the dressing. A notch will act as an in dication of fracture and reduce the force necessary for removing the tab member. As the fracture is controlled to proceed within a narrow intermediate zone the edges will become very smooth.

According to one embodiment of the invention the dressing is characterised in that the handle part has the carrier layer in common with the main part of the dressing, which renders it particularly easy to apply.

In another embodiment of the invention the dressing is characterised in that the handle part has the adhesive layer, the release liner and the carrier layer, optionally covered by a protective layer, in common with the main part of the dressing, which renders the dressing of the invention particularly easy to manufacture.

A further embodiment of the invention is characterised in that the handle part has the adhesive layer, the release liner and a protective layer, in common with the main part of the dressing. This embodiment is in practice particularly easy to manufacture, as the carrying layer may be added in line as e.g. an, in width precut, endless layer.

Yet another embodiment of the invention the dressing is characterised in that the handle part has the carrier layer and the adhesive layer in common with the main part of the dressing and is further provided with an additional layer and optionally covered by a protective layer. The additional layer is provided in order to prevent the tab member to stick to any surface e.g. the applying hand or finger. This embodiment renders it possible to use different materials for the additional layers of the tab members. This is e.g. an advantage in a wound dressing that is applied by a person suffering from motorical defects in the hands (e.g. rheumatism or Parkinson's ). In this case it is possible to use a stiff layer as the additional layer, which renders it much easier for such persons to apply the dressing.

It is preferred that the adhesive layer of the dressing is a skin friendly adhesive e.g. a PSA (Pressure Sensitive Adhesive) having water swelling properties. Especially is a skin friendly adhesive containing hydrocolloids preferred.

The dressing according to the invention may comprise emollients or an active constituent e.g. retinoids for treating or preventing formation of psoriasis, eczema, callous skin, corns, insect bites, acne or blisters. This opens for a medical treatment combined with an easy and uncontaminated application of the active ingredients. Further the dressing may have other properties as e.g. pressure relieving properties.

In a second aspect, the invention relates to a method for manufacturing discrete and individual dressings comprising a main part and a handle part, said main part comprising an adhesive layer, a release liner and a carrier layer optionally covered by a protective layer, wherein the handle part comprises at least one tab member, said tab member being designed for use as a grip for applying the dressing to the skin without touching the adhesive surface of the main part, and said tab member comprising one or more layers and having at least one layer in common with the main part of the dressing, said method comprising the steps of laminating a substantially continuous supply of the protective layer with a substantially continuous supply of the carrier layer, providing the carrier layer with an adhesive layer, providing a substantially continuous supply of the release liner, optionally cutting the protective layer and/or the release liner before or after lamination, bevelling the edges along the periphery and cutting the individual dressings. Such process is new and offers a very simple process for the manufacture of dressings according to the invention.

In a third aspect, the invention relates to a method for manufacturing discrete and individual dressings comprising a main part and a handle part, said main part comprising an adhesive layer, a release liner and a carrier layer optionally covered by a protective layer, wherein the handle part comprises at least one tab member, said tab member being designed for use as a grip for applying the dressing to the skin without touching the adhesive surface of the main part, and said tab member comprising one or more layers and having at least one layer in common with the main part of the dressing, said method comprising the steps of laminating a substantially continuous supply of the protective layer with a substantially continuous supply of the carrier layer, providing the carrier layer with an adhesive layer, providing a substantially continuous supply of an additional layer, providing a substantially continuous supply of the release liner, optionally cutting the protective layer and/or the release liner before or after lamination, bevelling the edges along the periphery of the individual dressings and cutting the individual dressings. The additional layer may be paper or film preventing the handle parts from sticking to any surface e.g. the applying hand or finger.

FIG. 1 illustrates an embodiment of a wound dressing 1 according to the invention, comprising a main part 2 and two tab members 3, 4. Between the tab members 3, 4 and the main part 2 of the dressing is two intermediate zones 7, 8. The dressing is provided with a notch 5, 6 in each of the two intermediate zones 7, 8. The dressing 1 comprises several layers 12, 13, 14 shown in common by the number 9. The notches 5, 6 are seen to influence more than one of the layers 9 of the dressing 1. When applying the dressing 1 the person grasp one of the two tab members and a release liner, not shown, is removed from at least the main part of the dressing, whereafter the person grasp both tab members 3, 4 and applies the main part 2 of the dressing on e.g. a wound. When the main part of the dressing is applied the two tab members are easily removed by pulling lightly. The tab members 3, 4 will then split from the main part 2 of the dressing leaving the edges smooth.

In the embodiment of FIG. 1 the notches are placed on the top side of the dressing. This is not meant to be limiting for the invention as the notches may be provided if appropriate, e.g. on the bottom side or on both the top and bottom side of the dressing. Further the dressing may be provided with several notches, e.g. three, four, five or more according to the use.

Figure 2:
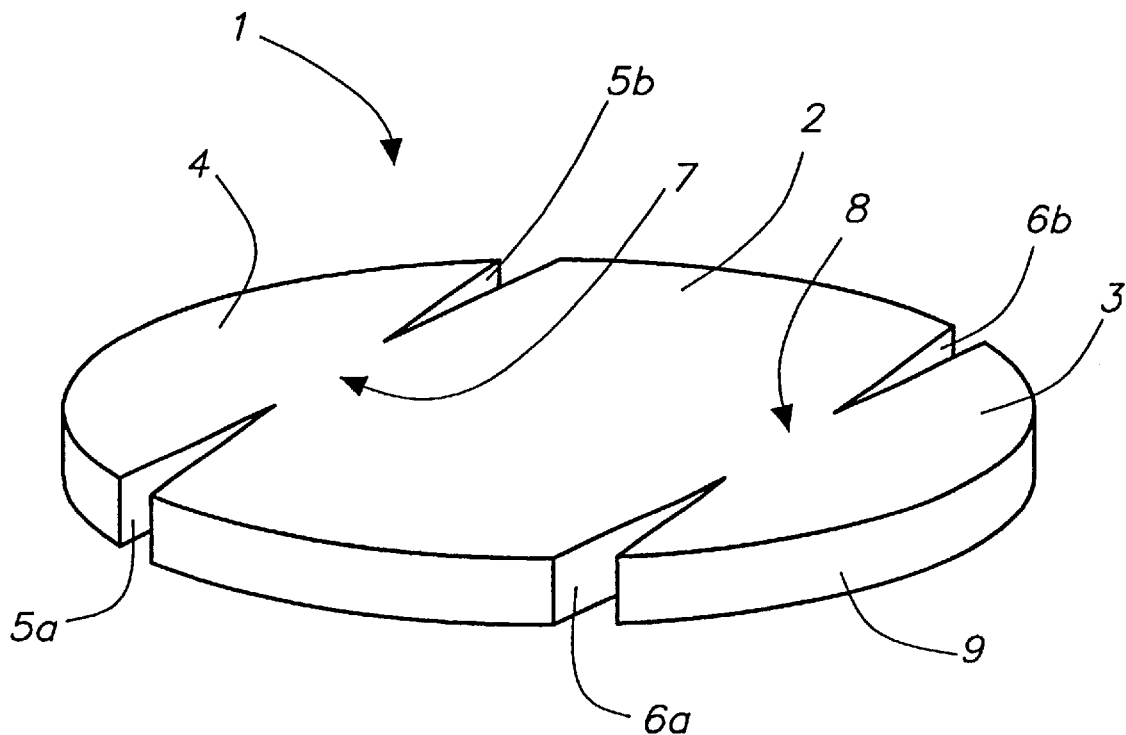
FIG. 2 and 3 are schematic views of two other embodiments of a wound dressing according to the invention each comprising two tab members and provided with two notches in each of the intermediate zones between the main part of the dressing and the two tab members.
Figure 3:
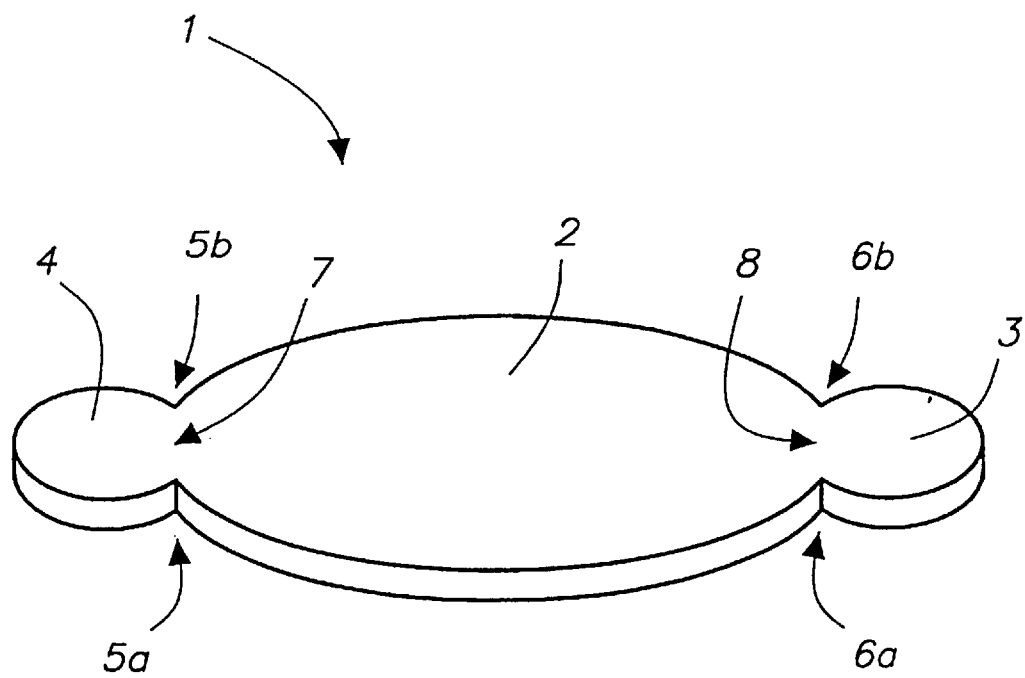

FIG. 2 and 3 illustrates two different embodiments of the dressing 1 of the invention comprising a main part 2 and two tab members 3, 4. Between the tab members 3, 4 and the main part 2 of the dressing is two intermediate zones 7, 8. The dressings are provided with two notches 5a, 5b and 6a, 6b in each intermediate zone 7, 8. These notches are provided through all the layers 9 of the dressing but not along the whole length of the two intermediate zones 7, 8. These two dressings are applied more or less in the same way as the dressing described above.

If notches are used, they can be provided as shown in the drawings, as combinations thereof or as any possibly combination according to the use or need.

The dressings according to the embodiments of the invention shown in the drawings may be bevelled in order to reduce the risk of the edges adhering to clothes and other things and thereby achieving a better overall adherence and furthermore to facilitate detaching of the tab member. Furthermore, it renders the dressing more conformable. The bevelling may be carried out in a way so that the thickness of the adhesive layer is smallest along the borders of the main part of the dressing and along the intermediate zones between the main part of the dressing and the tab members.

FIG. 4 to 7 illustrates schematically a sectional view of different embodiments of wound dressings having at least one tab member according to the invention. The dressing in each drawing comprises a main part 2, a tab member 3 and an intermediate zone 8 between the tab member 3 and the main part 2. A broken line 10 indicates in each drawing that only a part of the dressing is shown. The dressings comprise several layers, a protective layer 11, a carrier layer 12, an adhesive layer 13 and a release liner 14. The materials of the different layers may be any material applicable for the purpose of the specific layer.

Figure 4:
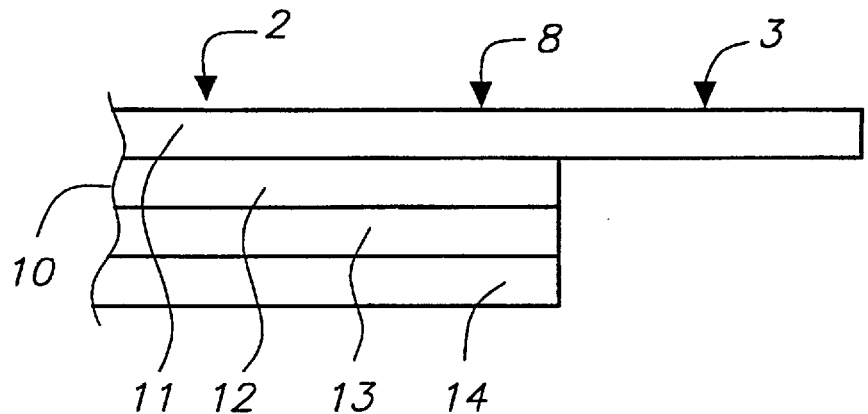
FIG. 4 illustrates schematically a sectional view of one side of a wound dressing having a tab member according to a first embodiment of the invention.

In FIG. 4 the tab member 3 consists of a single layer, the protective layer 11, which it has in common with the main part 2 of the dressing. In some embodiments the tab member 3 may be much larger, e.g. three to five times larger, than the main part 2 of the dressing 1.

Figure 5:
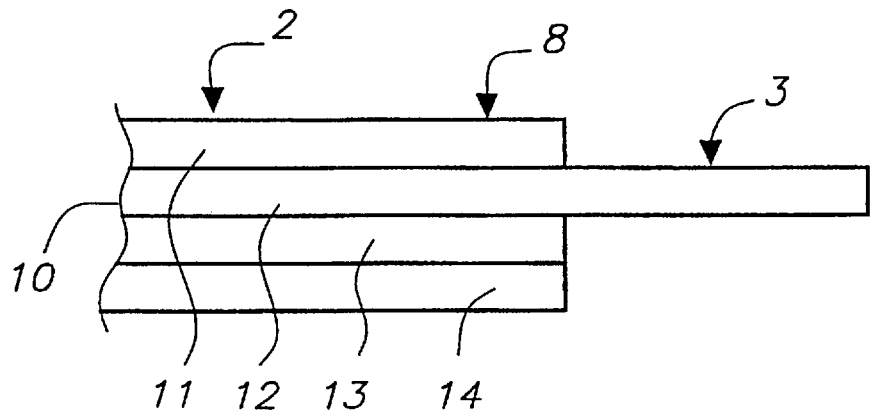
FIG. 5 illustrates schematically a sectional view of one side of a wound dressing having a tab member according to a second embodiment of the invention.

In FIG. 5 the tab member 3 consists of a single layer, the carrier layer 12, which it has in common with the main part 2 of the dressing.

In other embodiments the single layer could as well be e.g. the release liner.

Figure 6:
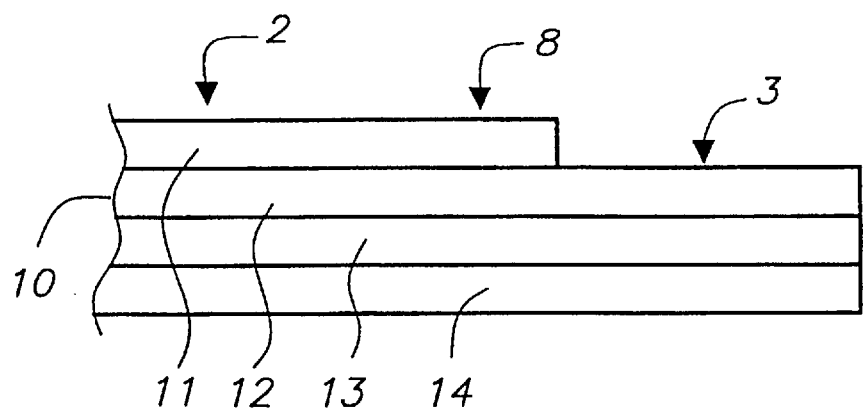
FIG. 6 illustrates schematically a sectional view of one side of a wound dressing having a tab member according to a third embodiment of the invention.

In FIG. 6 the tab member 3 is a laminate consisting of the carrier layer 12, the adhesive layer 13 and the release liner 14.

Figure 7:
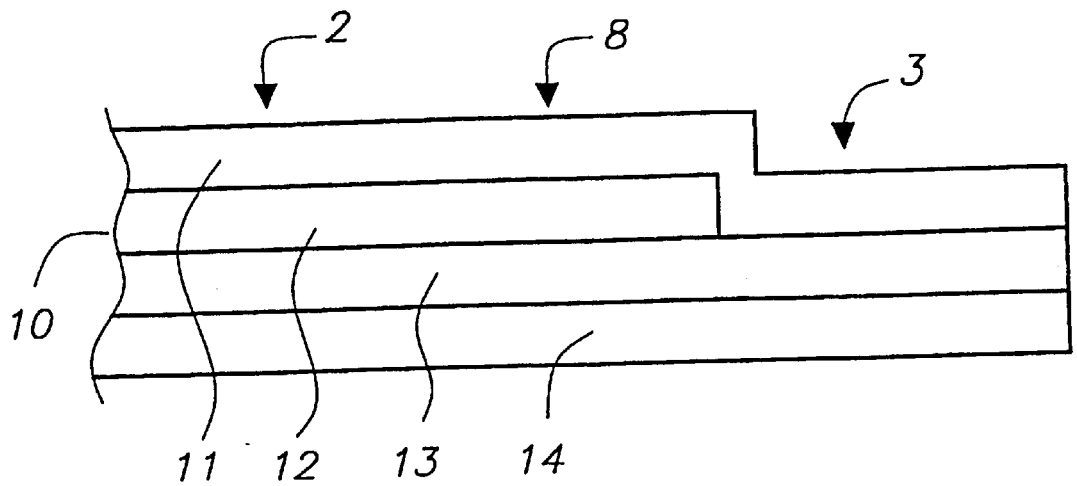
FIG. 7 illustrates schematically a sectional view of one side of a wound dressing having a tab member according to a fourth embodiment of the invention.

In FIG. 7 the tab member 3 is a laminate consisting of the protective layer 11 the adhesive layer 13 and the release liner 14. The adhesive layer 12 is limited to the main part 2 of the dressing and has its border in the intermediate zone 8.

Figure 8:
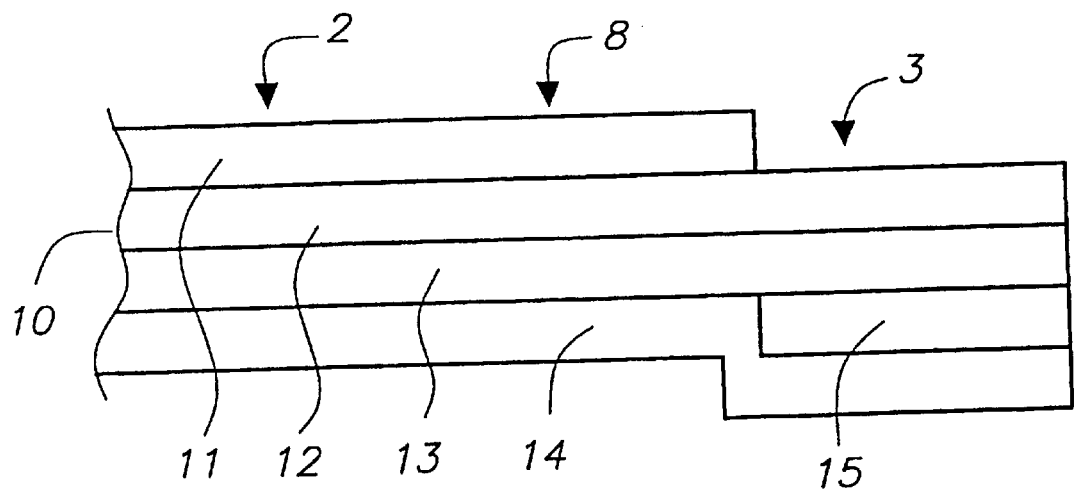
FIG. 8 illustrates schematically a sectional view of one side of a wound dressing having a tab member according to a fifth embodiment of the invention.

In FIG. 8 the tab member 3 is a laminate having three layers in common with the main part 2 of the dressing, the carrier layer 12, the adhesive layer 13 and the release liner 14. Further the tab member 3 is provided with an additional layer 15, and optionally covered by a not shown protective layer. The additional layer is provided in order to prevent the tab member to stick to any surface e.g. the applying hand or finger if the release liner is removed from the adhesive surface of both the main part 2 of the dressing and the tab member 3. The additional layer may be of any suitable material, e.g. a stiff material for facilitating handling of the dressing for people suffering from motorical defects in their hands or fingers.

The dressing may be provided with further additional layers.

Figure 9:
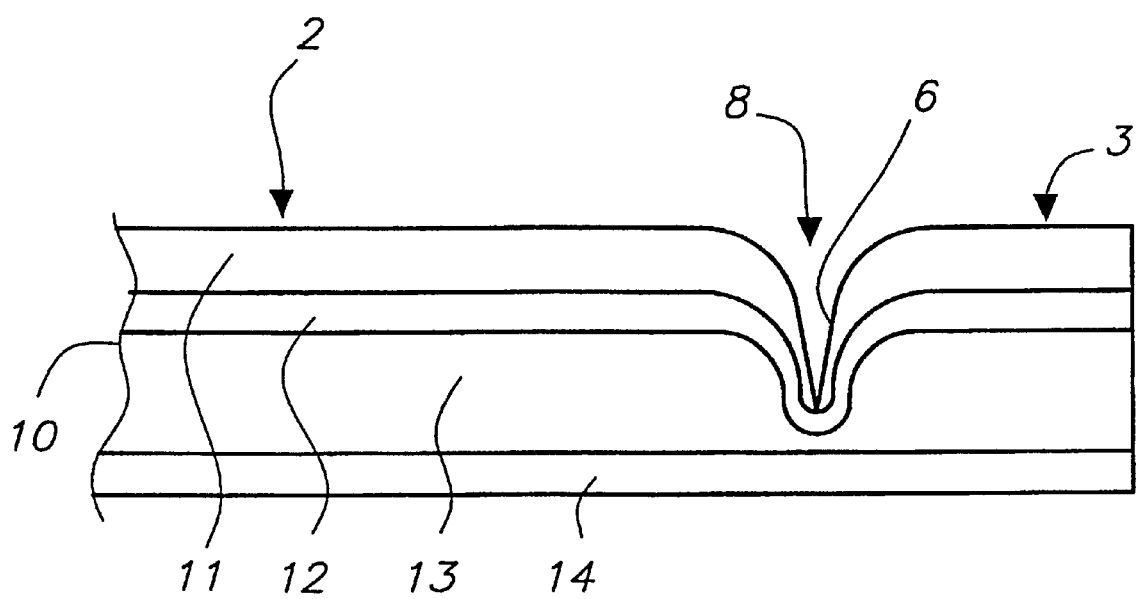
FIG. 9 illustrates schematically a sectional view of one side of a wound dressing having a tab member according to a sixth embodiment of the invention.

In FIG. 9 the tab member 3 is a laminate consisting of the protective layer 11, the carrier layer 12, the adhesive layer 13 and the release liner 14. The dressing is provided with a notch 6 in the intermediate zone 8 between the main part 2 and the handle part 3, the notch being cut through the protective layer 11. Further the adhesive layer 13 has a reduced thickness in the intermediate zone 8. This embodiment leaves very smooth edges when the handle part 3 is removed.

Figure 10:
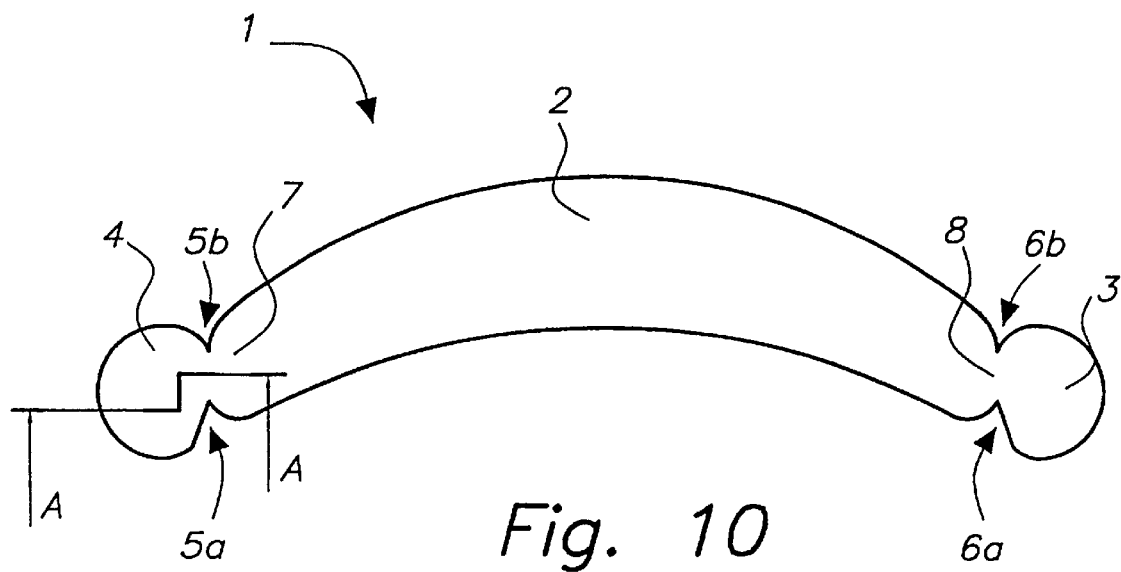
FIG. 10 is a schematic view of a "banana shaped" wound dressing according to the invention with two tab members and wherein a notch is provided along each of the intermediate zones between the main part of the dressing and the tab members.
Figure 11:
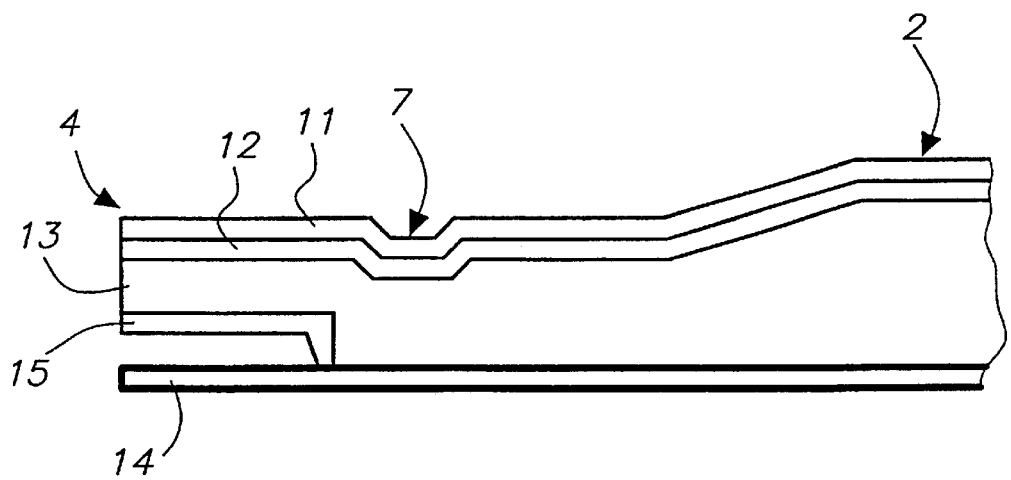
FIG. 11 illustrates schematically a sectional view along the line A—A of one side of the "banana shaped" wound dressing of FIG. 10.

FIG. 10 and FIG. 11 illustrates a "banana shaped" wound dressing 1 especially suitable for finger cracks. The wound dressing, according to the invention, comprises a main part 2 and handle parts 3, 4. Between the handle parts 3, 4 and the main part 2 of the dressing is two intermediate zones 7, 8. The dressing is provided with notches 5a, 5b, 6a, 6b in each of the two intermediate zones 7, 8. The dressing 1 comprises several layers as shown by the numbers 11, 12, 13, 14 and 15 in FIG. 11. When applying the dressing 1 the person removes the protective layer 11, grasps one of the two tab members and removes the release liner 14 from at least part of the main part of the dressing, whereafter the person grasps the handle parts 3, 4 and applies the main part 2 of the dressing on the finger crack on the finger tip, and applies the the two ends of the main part in a way so that it follows the contour of the fingernail smoothly. When the main part of the dressing is applied the two handle parts are easily removed by pulling lightly. The handle parts 3, 4 will then split from the main part 2 of the dressing leaving the edges smooth. When applying the dressing on the finger crack the two. ends close to the handle parts 3, 4 are applied on top of each other in order to further minimise the small area with a torn off edge. The "banana shape" has shown to be very efficient when applying a wound dressings on the finger tips.

As it is illustrated in FIG. 1 the intermediate zone 7 is made relatively thin during the bevelling process. During the bevelling process the adhesive layer 13 is provided with different thicknesses through the dressing. In this way the dressing is provided with more hydrophilic material close to the middle and less hydrophilic material along the edges, thus resulting in very thin edges.

MATERIALS AND METHODS

The materials of the layers of the dressings may be any suitable materials. Some materials are mentioned below, but are not meant to be limiting the possibly materials that can be used.

Methods for manufacturing the dressing according to the invention are any suitable methods known per se. Several conventional methods, e.g. punching, are described and used during long time and need not be giving any consideration here.

The choice of materials and methods for preparing a specific dressing according to the invention is easily made by the skilled in the art.

EXPERIMENTAL PART

The invention is explained more in detail below with reference to the Examples disclosing embodiments of the present invention. The examples are not considered to be limiting to the scope of the invention which is defined in the appended claims.

EXAMPLE 1

Preparation of a dressing equipped with a tab member according to the invention by punching a specific pattern of the dressing.

A dressing comprising a 30 μm Polyurethane carrier film, an adhesive layer containing hydrocolloids and a release liner (siliconised paper), which traditionally is punched as a rectangle, was punched in another design shown in FIG. 2 or 3 leaving an area which functioned as handles during application, whereafter said handles were easily removed by tearing.

EXAMPLE 2

Preparation of a dressing equipped with two tab members according to the invention by punching a specific pattern of the dressing combined with an additional layer between the adhesive layer and the release liner.

A dressing comprising a Polyurethane carrier film, an adhesive layer containing hydrocolloids and a release liner (siliconised paper), was manufactured as known per se, but during production two strips of additional liner were placed between the adhesive layer and the traditional release liner, a sectional view illustrates the laminate in FIG. 8. These additional liners prevented the tab members from adhering to the skin or to the applying finger. The dressing was punched in a design shown in FIG. 2 or 3, leaving an area which functioned as handles during application, whereafter said handles were easily removed by tearing.

EXAMPLE 3

Preparation of a dressing especially suitable for finger cracks.

A "banana shaped" dressing was designed according to FIG. 10 and FIG. 11. The dressing comprising a 15 μm Polyurethane carrier film, an adhesive layer containing hydrocolloids and a release liner, was manufactured as known per se. During production two strips of additional liner were placed between the adhesive layer and the traditional release liner in the area of the handle parts in order to preventing the handle parts from sticking e.g. to the applying hand. The "banana shaped" dressing was designed with two handle parts each separated from the dressing by two notches indicating a line of detachment.

The line of detachment is optimised, making it possible to stretch the dressing just enough to fit a fingertip during application, and yet feasible the following removal of the tab-members without detaching the dressing from the finger. The result is a dressing easy to apply to a fingertip, giving relief to the pain caused by the finger crack.

The invention has been described with reference to examples of specific embodiments thereof. Many modifications can be carried out without thereby deviating from the scope of the invention being defined by the scope of the appended claims.

What is claimed is:

1. A dressing comprising a main part having a periphery length, a handle part, and an intermediate zone between said main part and said handle part, said main part including an adhesive layer and a carrier layer, said handle part designed for use as a grip for applying the dressing to the skin without touching the adhesive layer of the main part and including one or more layers with at least one layer in common with the main part of the dressing, said intermediate zone having a length defined by a line of conjunction between the handle part and the main part which is less than 20% of said periphery length of the main part and including at least one notch, said main part having an upper surface which extends uninterrupted as a common layer over said intermediate zone without perforation.

2. The dressing as claimed in claim 1, wherein the handle part is provided with at least one additional layer.

3. The dressing as claimed in claim 1, wherein said notch is a cutout portion that extends through all the layers of the dressing but not along the entire length of said intermediate zone.

4. The dressing as claimed in claim 1, wherein the handle part includes the carrier layer of the main part of the dressing.

5. The dressing as claimed in claim 1, wherein the carrier layer is covered by a protective layer and the handle part includes the protective layer of the main part of the dressing.

6. The dressing as claimed in claim 1, wherein the handle part has the adhesive layer, the release layer and the carrier layer in common with the main part of the dressing.

7. The dressing as claimed in claim 6, wherein the carrier layer is covered by a protective layer and the handle part has the protective layer also in common with the main part of the dressing.

8. The dressing as claimed in claim 1, wherein the handle part has the carrier layer and the adhesive layer in common with the main part of the dressing and is further provided with an additional layer.

9. The dressing as claimed in claim 1, wherein said dressing comprises at least two handle parts, each handle part joined to said main part by a respective intermediate zone having a notch in a side thereof.

10. The dressing as claimed in claim 9, wherein each notch is a cutout portion that extends through all the layers of the dressing but not along the entire length of a respective intermediate zone.

11. The dressing as claimed in claim 1, wherein said dressing is bevelled along the periphery.

12. The dressing as claimed in claim 1, wherein said dressing has an elongated shape with a length to width ratio of at least 3:2.

13. The dressing as claimed in claim 1, wherein the main part comprises at least three protruding parts acting as three handle parts.

14. The dressing as claimed in claim 1, wherein the adhesive layer has water swelling properties.

15. The dressing as claimed in claim 1, said intermediate zone including two notches, one notch in each side of said intermediate zone, and an unnotched area between said two notches defining the length of said intermediate zone, each of said notches extending through all the layers of the dressing.

16. A dressing comprising a main part, a handle part, and an intermediate zone with a length defined by a line of conjunction between said main part and said handle part, said main part including an adhesive layer and a carrier layer, said handle part designed for use as a grip for applying the dressing to the skin without touching the adhesive layer of the main part and having at least one layer in common with the main part of the dressing, said intermediate zone including at least one notch in a side thereof so that the length of said intermediate zone is less than a widest portion of said handle part, said main part having an upper surface which extends uninterrupted as a common layer over said intermediate zone without perforation.

17. The dressing as claimed in claim 16, wherein said notch is a cutout portion that extends through all the layers of the dressing but not along the entire length of said intermediate zone.

18. The dressing as claimed in claim 16, said intermediate zone including two notches, one notch in each side of said intermediate zone, and an unnotched area defining the length of said intermediate zone extending between said two notches, each of said notches extending through all the layers of the dressing.

19. A dressing comprising a main part, a handle part, and an intermediate zone with a length defined by a line of conjunction between said main part and said handle part, said main part including an adhesive layer, a release liner and a carrier layer, said handle part designed for use as a grip for applying the dressing to the skin without touching the adhesive layer of the main part and having at least one layer in common with the main part of the dressing, said intermediate zone including at least one notch in a side thereof so that the length of said intermediate zone is less than a widest portion of said handle part, said main part having an upper surface which extends as a common layer over said intermediate zone without perforation, and said intermediate zone including two notches, one notch in each side of said intermediate zone, each of said notches extending through all the layers of the dressing but not along the entire length of said intermediate zone.

* * * * *

UNITED STATES PATENT AND TRADEMARK OFFICE
CERTIFICATE OF CORRECTION

PATENT NO. : 6,297,422 B1
DATED : October 2, 2001
INVENTOR(S) : Hansen et al.

Page 1 of 1

It is certified that error appears in the above-identified patent and that said Letters Patent is hereby corrected as shown below:

<u>Title page,</u>
Item [73], Assignee, the spelling of the name should be corrected from "Colorplast A/S" to -- Coloplast A/S --.

Signed and Sealed this

Second Day of April, 2002

Attest:

Attesting Officer

JAMES E. ROGAN
*Director of the United States Patent and Trademark Office*